United States Patent [19]

Yukl

[11] 4,327,322
[45] Apr. 27, 1982

[54] BIDIRECTIONAL CURRENT SUPPLY CIRCUIT

[75] Inventor: Tex N. Yukl, Banks, Oreg.

[73] Assignee: Spatial Dynamics, Ltd., Beaverton, Oreg.

[21] Appl. No.: 194,339

[22] Filed: Oct. 6, 1980

[51] Int. Cl.³ .......................... A61N 1/36; G05F 3/02
[52] U.S. Cl. ................................... 323/351; 128/421; 323/271
[58] Field of Search ............................ 128/421, 423 R; 323/268, 270, 271, 350, 351; 363/131, 132

[56] References Cited

U.S. PATENT DOCUMENTS 3,233,161  2/1966  Sikorra ............................ 323/350 X
3,924,641  12/1975 Weiss ................................... 128/421
4,102,347  7/1978  Yukl ..................................... 128/421

Primary Examiner—A. D. Pellinen
Attorney, Agent, or Firm—Kolisch, Hartwell & Dickinson

[57] ABSTRACT

A bidirectional current supply circuit for nerve stimulation including current-level adjusters and a mode switch having two operating conditions. One condition provides for operation solely with one adjuster in series circuit for common control of the level of current flowing in opposite directions through a load connected to the circuit. The other condition provides for operation with a pair of adjusters substantially in parallel circuit with each other for independent level-control of current flowing in reverse directions through a load.

4 Claims, 4 Drawing Figures

BIDIRECTIONAL CURRENT SUPPLY CIRCUIT

BACKGROUND AND SUMMARY OF THE INVENTION

This invention pertains to a bidirectional current supply circuit, and more particularly, to such a circuit which includes adjusters which enable independent-level-control of current flowing in reverse directions through a load connected to the circuit. For the purpose of illustration herein, a preferred embodiment of the circuit is described in connection with transcutaneous nerve stimulation which is used for pain relief purposes.

A conventional bidirectional current supply circuit, similar to that disclosed in U.S. Pat. No. 4,102,347, entitled "Electronic Pain Control System", includes a single adjuster for controlling the level of current flowing through a load connnected to the circuit. Thus, the current flowing in reverse directions is always of the same level.

While there are applications for which this kind of an arrangement is entirely satisfactory, there are others where it is desirable to apply current in reverse directions of different levels. One of these applications concerns devices known as transcutaneous nerve stimulators which, essentially, are pulsed current supply circuits intended for connection through a pair of electrodes to a person's skin for the purpose of creating electrical current nerve stimulation. Such a device is used quite frequently for pain relief.

Nerves have a polarization characteristic such that negative-going pulses—that is, when the electrode over the pain site is a cathode—provide substantially more effective stimulation than positive—going pulses. If a person has a single pain site, the conventional common level-control current supply circuit provides the necessary pain relief. However, when a person has two areas of pain, the conventional circuit requires that two pairs of electrodes be used. This is necessary because different nerve sites require different levels of stimulation.

A general object of the present invention is to provide a bidirectional current supply circuit which includes independent-level-control of current flowing in reverse directions through a load connected to the circuit and a mode switch for optional operation with common-level-control.

More particularly, the present invention proposes a circuit wherein level control is provided by adjusters arranged substantially in parallel circuit with each other, and a switch, connected in series with the adjusters and the circuit, having a pair of switch conditions, one of which provides for common level-control of current flowing in reverse directions, similar to that provided in a conventional circuit, and the other of which provides for operation with independent current level-control.

With this kind of arrangement, a person, through the use of only two electrodes, can provide pain relief at either one site or concurrently at two sites. The relief of pain at two sites is thus provided, as far as the person operating the circuit is concerned, with only the addition of a mode switch and an additional adjuster.

These and other objects and advantages which are attained by the invention will become more fully apparent as the description which now follows is read in conjunction with the accompanying drawings.

DETAILED DESCRIPTION OF THE INVENTION

Figure 1:
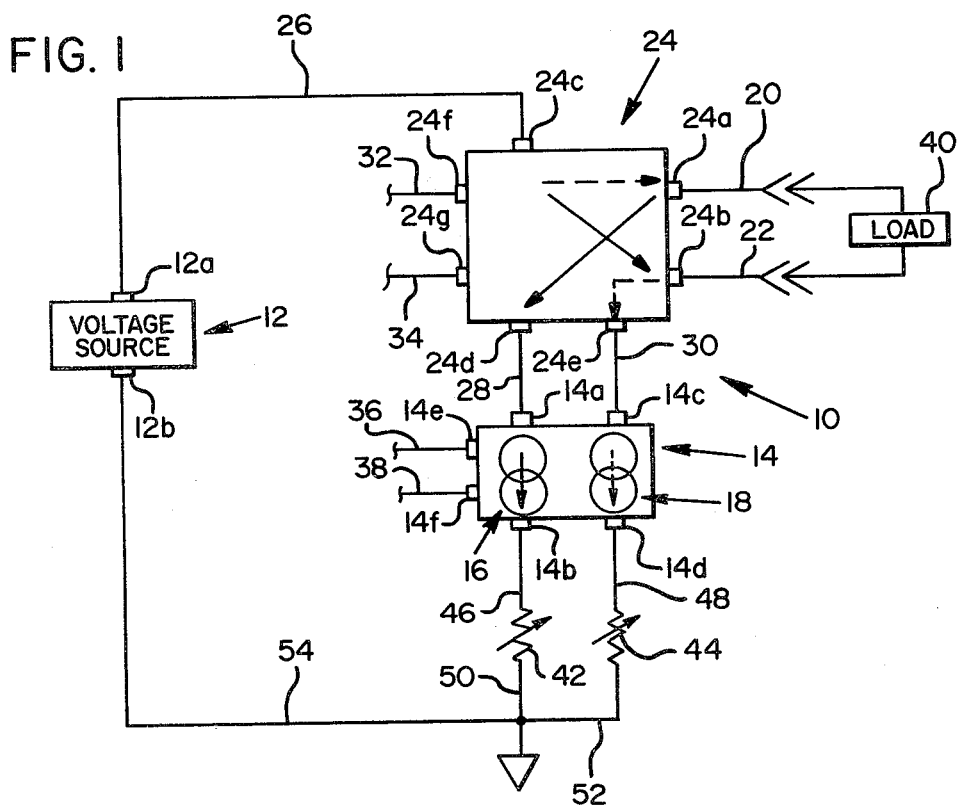
FIG. 1 is a schematic diagram, partly in block form, illustrating the construction of a portion of a transcutaneous nerve stimulator including a current supply circuit constructed in accordance with the present invention.

Turning now to FIG. 1, indicated at 10 is a portion of a transcutaneous nerve stimulator including a current supply circuit constructed in accordance with the present invention. Shown in block form at 12 is a conventional voltage source which produces, between terminals 12a, 12b, a DC output voltage that typically ranges between about 10-volts DC and about 100-volts DC. Terminal 12b is connected to circuit ground by a conductor 54.

A conventional controlled changeable-direction current source is indicated in block form at 14. Shown within block 14, schematically, are symbols representing two current generators 16, 18, wherein arrows are used to indicate the respective orientations for producing current flow. A solid arrow is used in generator 16, and a dashed-arrow in generator 18. When generator 16 is switched on, as will be explained, it couples to output terminals 14a, 14b, in block 14. Similarly, when generator 18 is switched on, it couples to output terminals 14c, 14d.

It should be understood that while source 14 as just described includes a pair of similarly directed current generators, such an arrangement could also be constructed using a single generator, with appropriate switching circuitry provided which effectively changes the terminals through which current flows. There are many ways of constructing such a source, and none of them forms any part of the present invention.

Control terminals 14e, 14f are provided for block 14. With a certain positive voltage existing on terminal 14e generator 16 operates. With essentially the same certain positive voltage existing on terminal 14f generator 18 operates.

Further included in circuit 10 and two output terminals 20, 22. Terminal 20 is connected to a terminal 24a in a switching circuit 24, the function of which will be explained shortly. Terminal 22 is connected to a terminal 24b of the switching circuit. A terminal 24c of circuit 24 is connected to source 12 by a conductor 26. Terminals 24d, 24e of circuit 24 are respectively connected to terminals 14a, 14c of source 14 by means of conductors 28, 30, respectively.

Switching of circuit 24 is controlled through terminals 24f, 24g. With a certain positive voltage existing on terminal 24f, and a substantially 0-voltage existing on terminal 24g, terminal 24c is effectively connected to terminal 24b, and terminal 24a is so connected to terminal 24d as shown by the solid-arrows. In the reverse case where positive voltage is on 24g and a 0-voltage on terminal 24f, terminal 24c is connected to terminal 24a, and terminal 24b is connected to terminal 24e, as shown by the dashed-arrows.

Further explanation of the preferred embodiment will be facilitated by identifying at this point the connections of the control terminals in the current supply circuit. Terminal 24f is connected to a conductor 32, and terminal 24g is connected to a conductor 34. Current source control terminal 14e is connected to a conductor 36, while terminal 14f is connected to a conductor 38.

Terminals 20, 22, previously described, are adapted for connection, through suitable body-contacting electrodes, to a person's skin, represented in the figure by block 40 designated "LOAD".

Further contained in circuit 10, in accordance with the invention, is a pair of independent level-control adjusters, 42, 44, also referred to herein as current level control means. Adjuster 42, represented in FIG. 1 as a variable resistor, is connected to terminal 14b of source 14 by means of a conductor 46. Similarly, adjuster 44, also shown as a variable resistor, is connected to terminal 14d by means of a conductor 48. Adjusters 42, 44 are connected to circuit ground by means of conductors 50, 52, respectively.

In the setting of transcutaneous nerve stimulation, it has been found to be desirable to supply a current to a patient in pulses at a rate of around 100-pulses-per-second. More specifically, it has been found to be desirable to apply, first, a pulse of one polarity for a selected time duration, such as about 0.2-milliseconds, followed immediately by an equal current pulse in the opposite direction for substantially the same duration—with such "bidirectional" pulses applied at the above-mentioned rate. In the circuit shown in FIG. 1, the required current control may be provided by a conventionally constructed pulse generator or similar device providing appropriate control pulses on terminals 24f, 24g, 14e, 14f.

Figure 4:
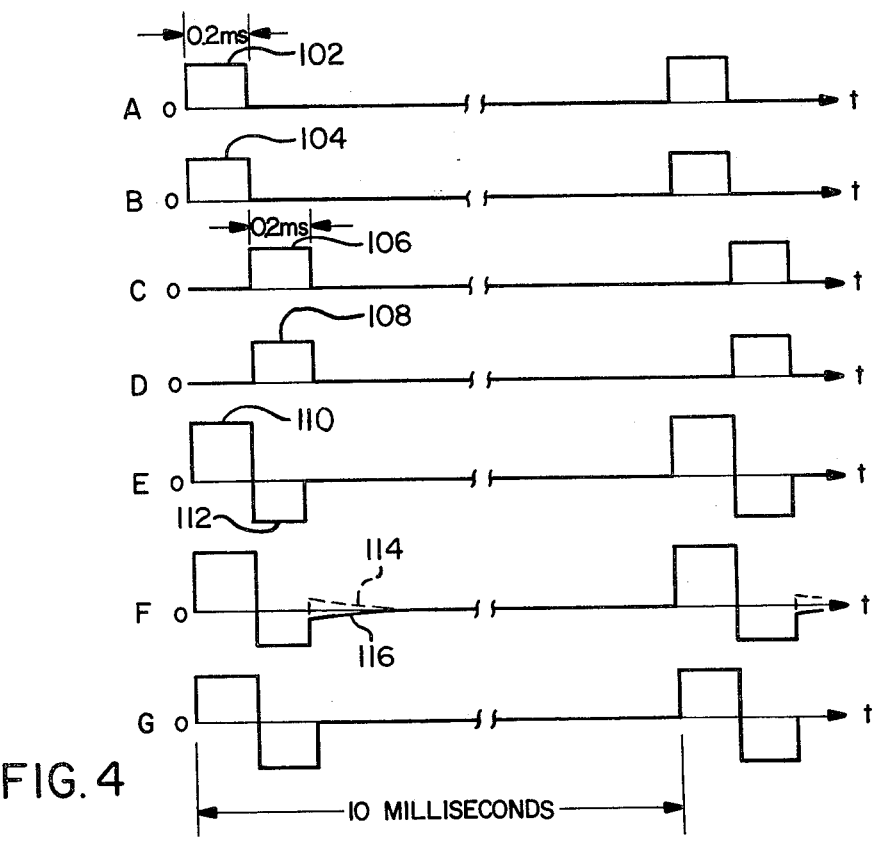
FIG. 4 is a sketch showing on a common time base idealized wave forms of voltages used to control the current supply circuit, and of currents resulting in a load connected to the circuit.

Explaining how the various elements of the supply circuit cooperate to produce the desired current in a load, reference is made to FIG. 4 which shows various wave forms of voltages and currents which appear at different locations in circuit 10. A voltage pulse depicted in wave form A at 102 is applied to control terminal 24f, while a similar voltage pulse, shown in wave form B at 104, is applied to control terminal 14e. When pulses 102, 104 are applied simultaneously to terminals 24f, 14e, respectively, current generator 16 turns on to produce current flow through adjuster 42, through conductors 50, 54, voltage source 12, and through conductor 26 and switching circuit 24. As previously described, a positive voltage applied to terminal 24f, causes terminal 24c to be connected to terminal 24b, and terminal 24a to be connected to terminal 24d. Thus, current flows from output terminal 22 through the load and back into current source 14 through terminal 20.

During the next phase of an operating cycle, the voltage levels on terminals 24f, 14e return to "0", and the voltage levels on terminals 24g, 14f become positive. Again referring to FIG. 4, wave forms C and D at 106, 108, respectively, represent the voltages applied to terminals 24g, 14f. This situation causes current source 18 to operate. In this case current now flows through adjuster 44, through voltage source 12 by way of conductors 52, 54, and again into switching circuit 24 by means of conductor 26. With terminal 24c now connected to terminal 24a, and with terminal 24b connected to terminal 24e, due to the positive voltage on conductor 24g, current flows in the reverse direction through the load.

During the remainder of the cycle, the voltage level on all four control terminals is "0". The resulting current wave form through the load is illustrated by wave form E of FIG. 4. Since adjuster 42 has current flowing through it only during the time that current is flowing upwardly through the load in FIG. 1, which will hereinafter be referred to as a positive current, its manipulation does not affect the level of current flowing in the reverse direction. Similarly, adjuster 44 only affects the current level flowing in the reverse or negative direction. One can thus see that the level of current flowing through the load in the opposite directions is controlled independently by the two adjusters. An idealized depiction of the resulting load current is shown in the wave form identified as E in FIG. 4, wherein the positive going current, shown at 110, is of a higher value than the negative going current shown at 112.

Figure 2:
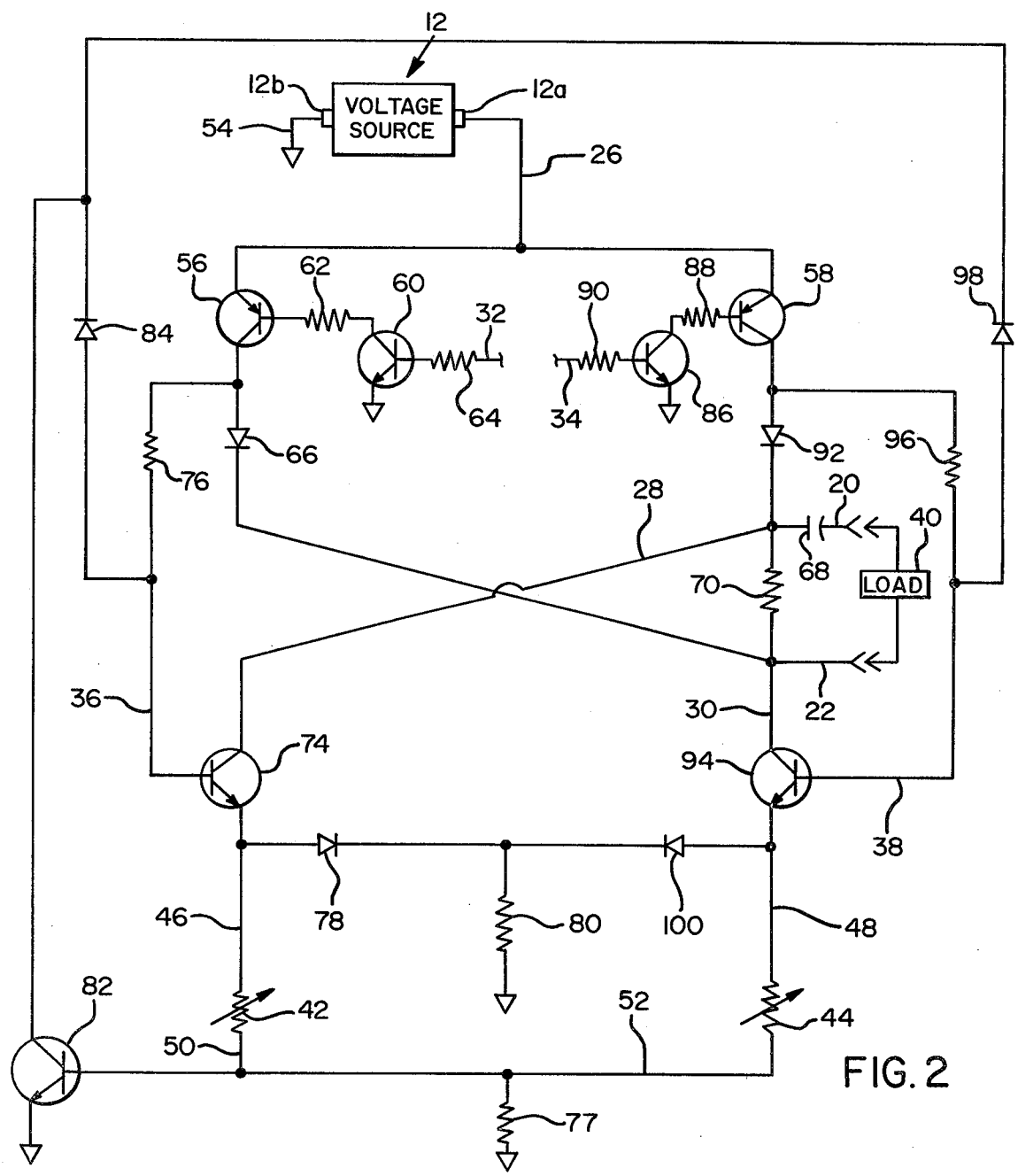
FIG. 2 is a circuit diagram, partly in block form, illustrating a preferred construction of the current supply circuit shown in FIG. 1.

FIG. 2 illustrates a more detailed circuit diagram of the preferred embodiment of this invention. The circuit is divided into two essentially parallel circuits providing current flow in each direction through the load. Beginning with voltage source 12 shown at the top of the figure, terminal 12b again is connected to the circuit ground while terminal 12a is connected to the emitters of two transistors 56, 58. The base of transistor 56 is connected to the collector of a transistor 60 through a resistor 62. The emitter of transistor 60 is grounded, and the base is connected to previously mentioned control input conductor 32 through a resistor 64.

The collector of transistor 56 is connected through a diode 66 to output terminal 22. As discussed previously, load 40 is connected to the circuit at terminals 22, 20. A capacitor 68 is connected in series with load 40 between terminal 20 and conductor 28 and a resistor 70 is connected in parallel between terminal 22 and conductor 28. The junction of capacitor 68 and resistor 70 is connected via conductor 28 to the collector of a transistor 74. The base of transistor 74 is connected through a resistor 76 to the junction between the collector of transistor 56 and diode 66. The emitter of transistor 74 is connected to conductor 46 which, as discussed previously, connects to adjuster 42. Adjuster 42 is connected through a resistor 77 to the circuit ground. The junction between the emitter of transistor 74 and adjuster 42 is connected through a diode 78 and a resistor 80 to circuit ground. The junction between adjuster 42 and resistor 77 is connected to the base of a transistor 82, the emitter of which is grounded. The junction between resistor 76 and the base of transistor 74 is connected through a diode 84 to the collector of transistor 82. This completes the circuitry necessary to provide a current flowing in the positive direction through the load controllable by adjuster 42.

As stated previously the emitter of transistor 58 is connected to the voltage source through conductor 26. The base of transistor 58 is connected to the collector of a transistor 86 through a resistor 88, the emitter of transistor 86 being grounded. Input control conductor 34 is connected to the base of transistor 86 through a resistor 90. The collector of transistor 58 is connected through a diode 92 to the junction of capacitor 68 and resistor 70. Output terminal 22 is connected to the collector of a transistor 94 through conductor 30. The junction between the collector of transistor 58 and diode 92 is connected through a resistor 96 to the base of transistor 94. The junction between resistor 96 and the base of transistor 94 is connected through a diode 98 to the collector of transistor 82.

The emitter of transistor 94 is connected to conductor 48, which, as discussed previously, is connected to adjuster 44. Adjuster 44 is connected by conductor 52 through resistor 77 to circuit ground. The junction between the emitter of transistor 94 and adjuster 44 is connected through a diode 100 in series with resistor 80 to circuit ground.

Explaining operation of the circuit with voltage source 12 in operative condition, a positive pulse is applied on conductor 32 at the beginning of the cycle, as shown on wave form A in FIG. 4 at 102. This turns transistor 60 on which causes current to flow in resistor 62 raising the voltage level of the base of transistor 56 turning it on and causing a positive pulse to occur at the base of transistor 74, as shown at 104 on wave form B in FIG. 4, which turns it on. This results in current flowing through diode 66, through output terminal 22, through the load and back via conductor 28 through transistor 74. Most of the current flowing through transistor 74 passes through diode 78 and from there into circuit ground through resistor 80. The remainder of the current flows through adjuster 42 and down through resistor 77 to circuit ground. Adjustment of adjuster 42 varies the amount of current flowing through the load. Currents ranging between 0 and 30 milliamps have been shown to be most useful for pain relief in transcutaneous nerve stimulators. The circuit is typically set for a current of approximately 10-milliamps.

When current flows in conductor 50, the base of transistor 82 is raised turning the transistor on. This results in current flow through diode 84, thereby reducing the voltage level of the base of transistor 74. This limits the conduction of transistor 74 to a desired current level.

The resulting wave form of the current passing through the load for this first portion of the cycle is shown on wave form E of FIG. 4 at 110 in an idealized state.

During the next portion of the cycle, control conductor 32 returns to a "0" level of voltage potential, and control conductor 34 increases to a positive potential level, such as is illustrated on wave form C of FIG. 4 at 106. As a result, transistor 86 turns on causing the base of transistor 58 to have a positive voltage level which transistor is thereby also turned on. The connection of the collector of transistor 58 with the base of transistor 94 through resistor 96 raises the base voltage level of transistor 94, as shown at 108 on wave form D of FIG. 4, causing that transistor to conduct. Current therefore, begins to flow through diode 92 and terminal 20 to the load, and back to conductor 30 and to the collector of transistor 94.

As was the case with transistor 74 during the first phase of the cycle, the voltage level of the base of transistor 94 is maintained at a desirable level through conduction of current through diode 98 and transistor 82 to ground.

The current flowing out of the emitter of transistor 94 goes primarily through diode 100 and resistor 80 to ground. However, a portion of the current also flows through adjuster 44 and resistor 77 to ground. Adjustment of adjuster 44 provides for the setting of the desired load current level for effective pain relief. Wave form E of FIG. 4 at 112 illustrates the negative-going pulse.

The voltage level of conductors 32, 34 is maintained at a "0" level during the remainder of the cycle. Thus, the load receives a positive current for a duration of approximately 0.2-milliseconds followed immediately by a negative current of the same duration, and then "0" current for approximately 9.6-milliseconds before a new pulse is generated.

As mentioned previously, the load-current wave form shown as E on FIG. 4, is an idealized representation. In fact, a more correct representation is shown by wave form F in FIG. 4, wherein, due to the unbalanced level of the reverse current levels, a residual DC current results, as shown by the dashed line at 114. Depending on the magnitude of this DC current level, an irritation of the skin of the person using the transcutaneous nerve stimulator can result. The addition of capacitor 68 in series with the load, and resistor 70 in parallel with the load causes a current flow as shown by solid line 116 in wave form F, thereby erasing the residual DC current. If the levels of the reverse direction currents are equal, as is the case in conventional transcutaneous nerve stimulators, there is no residual DC current, and the R-C coupling provided by capacitor 68 and resistor 70 is not required. A current of this type is shown as wave form G in FIG. 4.

Figure 3:
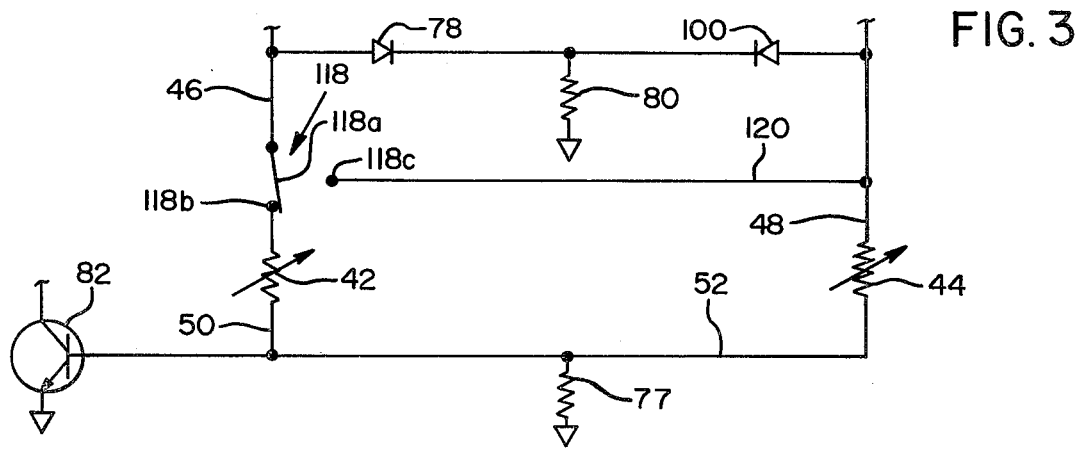
FIG. 3 is a fragmentary circuit diagram illustrating a portion of the circuit illustrated in FIG. 2 modified to include a mode switch providing for either common or independent level-control of reverse currents.

As discussed previously, the circuits shown in FIGS. 1 and 2, are useful where it is desirable to provide transcutaneous nerve stimulation to two areas of a person's body. However, if the person has only one site of pain, it is desirable to have reverse direction currents of equal levels. A circuit providing the capability of choosing between two modes of operation, one of which provides for independent current-level control where two pain sites exist, and the other of which provides for common current-level control when only one pain site exists, is illustrated in the fragmentary circuit diagram of FIG. 3. In this circuit a switch 118 is connected as shown just above adjuster 42. Switch 118 includes a blade 118a, and two contacts 118b, 118c. The switch is shown in a condition with blade 118a connecting resistor 42 to conductor 46 through contact 118b. With the switch in this condition, the circuit modification shown in FIG. 3 performs in exactly the same manner as the circuit illustrated and described with reference to FIG. 2. When blade 118a connects with contact 118c which is connected to conductor 48 through a conductor 120, a single-site single-adjustment mode of operation is provided. In this condition, adjuster 44 controls the level of current flowing in both directions. The combination of switch 118, also herein referred to as switching means, and adjusters 42, 44, constitutes dual-operating-mode current-level control means herein.

There is thus provided by the invention a unique current supply circuit in which independent level control of current in reverse directions is provided. Additionally, capability is provided to choose between a pair of independent level-control adjusters or a single, common level-control adjuster.

It will be appreciated that the circuit of the invention may be used in a number of applications other than in the setting of a transcutaneous nerve stimulator. Additionally, it can be seen that modifications of the circuit to vary the frequency, level or other characteristics of the load-current wave form are possible within this invention.

Thus, while a preferred embodiment of the invention has been described herein, it is appreciated that variations and modifications may be made without departing from the spirit of the invention.

It is claimed and desired to secure by Letters Patent:

1. A current supply circuit comprising
a pair of output terminals adapted for connection to a load,
a controlled changeable-direction current source operatively connected to said terminals for supplying current to a load connected therebetween, and
current control means operatively connected to said source, and therethrough to said terminals, for enabling independent adjusting of the level of current flowing in each of the two possible directions through such load via said terminals.

2. The circuit of claim 1, wherein said control means includes a pair of independent level-control adjusters.

3. A current supply circuit comprising
a pair of output terminals adapted for connection to a load,
a controlled changeable-direction current source operatively connected to said terminals for supplying current to a load connected therebetween, and
dual-operating-mode current-level control means operatively connected to said terminals through said source for enabling, selectively, operation of the current supply circuit in one mode where common-level control is provided for current flow in reverse directions, and in another mode where independent-level control is provided for such flow in reverse directions.

4. A current supply circuit comprising
a pair of output terminals adapted for connection to a load,
a controlled changeable-direction current source operatively connected to said terminals for supplying current to a load connected therebetween, and
dual-operating-mode current-level control means operatively connected to said terminals through said source for enabling, selectively, operation of the current supply circuit in one mode where common-level control is provided for current flow in reverse directions, and in another mode where independent-level control is provided for such flow in reverse directions,
said control means including a pair of adjusters, and switching means operatively connected to said adjusters, said switching means having a pair of switch conditions, one of which effects placement of the control means in said one mode with only one of the two adjusters operatively connected to said terminals through said source whereby current level control is controlled in reverse-flow directions solely by said one adjuster, and the other of which effects placement of the control means in said other mode with said two adjusters operatively interactive with one another in such a manner that each adjuster independently effects current-level control in reverse-flow directions.

* * * * *